(12) United States Patent
Sabata (10) Patent No.: US 8,641,624 B2
(45) Date of Patent: Feb. 4, 2014

(54) ULTRASOUND DIAGNOSTIC APPARATUS

(75) Inventor: Tomohiro Sabata, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 607 days.

(21) Appl. No.: 12/401,826

(22) Filed: Mar. 11, 2009

(65) Prior Publication Data

US 2009/0240151 A1 Sep. 24, 2009

(30) Foreign Application Priority Data

Mar. 18, 2008 (JP) .................................. 2008-069981

(51) Int. Cl.
*A61B 8/00* (2006.01)

(52) U.S. Cl.
USPC ............................ 600/444; 600/407; 600/437

(58) Field of Classification Search
USPC ......... 600/407, 437, 442, 443, 444, 445, 447, 600/459; 601/2; 73/609, 610, 612, 618, 73/620, 624, 625, 627, 633
See application file for complete search history.

(56) References Cited

U.S. PATENT DOCUMENTS

| | | | | |
|---|---|---|---|---|
| 4,584,880 | A * | 4/1986 | Matzuk | 73/609 |
| 4,811,740 | A * | 3/1989 | Ikeda et al. | 600/437 |
| 4,957,100 | A * | 9/1990 | Herzog et al. | 601/2 |
| 5,318,027 | A * | 6/1994 | Fukui | 600/437 |
| 5,462,058 | A * | 10/1995 | Yamada et al. | 600/454 |
| 6,468,213 | B1 | 10/2002 | Knell et al. | |
| 6,500,126 | B1 * | 12/2002 | Brock-Fisher | 600/459 |
| 7,078,668 | B2 * | 7/2006 | Yamazaki et al. | 250/208.1 |
| 2003/0133049 | A1 * | 7/2003 | Cowley et al. | 348/731 |
| 2005/0203402 | A1 | 9/2005 | Angelson et al. | |
| 2006/0173306 | A1 * | 8/2006 | Matsumura et al. | 600/437 |
| 2006/0241490 | A1 * | 10/2006 | Lazenby | 600/472 |
| 2007/0232924 | A1 * | 10/2007 | Karasawa | 600/459 |
| 2007/0239001 | A1 * | 10/2007 | Mehi et al. | 600/437 |

FOREIGN PATENT DOCUMENTS

| | | |
|---|---|---|
| JP | 10-033533 | 2/1998 |
| JP | 10-290799 | 11/1998 |
| JP | 2004-194981 | 7/2004 |
| JP | 2004-258533 | 9/2004 |
| JP | 2005-230378 | 9/2005 |
| JP | 2006-204560 | 8/2006 |
| JP | 2006-230919 | 9/2006 |

OTHER PUBLICATIONS

Japanese Office Action dated Dec. 8, 2009.

* cited by examiner

*Primary Examiner* — James Kish
*Assistant Examiner* — Michael N Fisher
(74) *Attorney, Agent, or Firm* — Scully, Scott, Murphy & Presser, P.C.

(57) ABSTRACT

An ultrasound diagnostic apparatus includes a connection section to which an ultrasound probe having an ultrasound transducer mounted therein is detachably connected, a transmission section that drives the ultrasound transducer of the ultrasound probe connected to the connection section by a transmission signal of a transmission frequency thereof, an echo signal creation section that creates a digital echo signal from an echo signal received by the ultrasound transducer, a signal processing section that carries out signal processing to the digital echo signal, a processing-speed changing section that changes an operation frequency of the signal processing in the signal processing section, and a change control section that controls change of the operation frequency.

6 Claims, 7 Drawing Sheets

ULTRASOUND IMAGE

ULTRASOUND DIAGNOSTIC APPARATUS

CROSS REFERENCE TO RELATED APPLICATION

This application claims benefit of Japanese Application No. 2008-069981 filed in Japan on Mar. 18, 2008, the contents of which are incorporated by this reference.

BACKGROUND OF THE INVENTION

1. Field of the Invention

The present invention relates to an ultrasound diagnostic apparatus having a common signal processing section that can process both data of an electronic scan ultrasound probe and a mechanical scan ultrasound probe connected thereto.

2. Description of the Related Art

Traditionally, an ultrasound diagnostic apparatus repeatedly transmits an ultrasound pulse from an ultrasound transducer of an ultrasound probe connected thereto to a living tissue, receives an echo signal of the ultrasound pulse reflected from the living tissue, creates information in the living body as a visible image of an ultrasonotomographic image and displays the image on a display section such as a monitor and the like.

To such an ultrasound diagnostic apparatus, various types of ultrasound probes are connected according to observation sites and diagnosis applications. For example, to the above ultrasound diagnostic apparatus, both a detachable electronic scan ultrasound probe and a mechanical scan ultrasound probe might be connected.

The electronic scan ultrasound probe is an electronic-scan type ultrasound probe that scans inside a body cavity by electrically driving an ultrasound transducer mounted inside. The mechanical scan ultrasound probe is a mechanical-scan type ultrasound probe that scans inside the body cavity by mechanically rotating the ultrasound transducer mounted inside.

Such an ultrasound diagnostic apparatus transmits a pulse-state ultrasound wave from the ultrasound transducer of the ultrasound probe connected thereto, receives the pulse-state ultrasound wave reflected from a portion where an acoustic impedance of the living tissue changes and converts the ultrasound wave to an echo signal. Also, the ultrasound diagnostic apparatus has a signal processing section that carries out signal processing required for creating an ultrasonotomographic image to the received echo signal.

For example, Japanese Patent Application Laid-Open Publication No. 10-290799 as a first prior art discloses an art relating to an ultrasound diagnostic apparatus, which is an ultrasound diagnostic apparatus that can handle both electronic scan and mechanical scan, having processing means and the like in which an analog received signal obtained in an electronic scan mode is converted by an A/D converter to digital data and then, the digital data and a coefficient are integrated.

Also, Japanese Patent Application Laid-Open Publication No. 2005-230378 as a second prior art discloses an art relating to a connection adapter for ultrasound observing device, which is an ultrasound observing device made capable of electronic ultrasound scan by connecting an electronic scan ultrasound probe to an ultrasound observing device to which a mechanical scan ultrasound probe is connected and carries out digital signal processing by a scan converter through digital conversion of a received signal from the electronic scan ultrasound probe using an A/D converter.

SUMMARY OF THE INVENTION

An ultrasound diagnostic apparatus according to an embodiment of the present invention includes a connection section to which an ultrasound probe having an ultrasound transducer mounted therein is detachably connected;
a transmission section that drives the ultrasound transducer of the ultrasound probe connected to the connection section by a transmission signal of a transmission frequency thereof;
an echo signal creation section that creates a digital echo signal from an echo signal received by the ultrasound transducer and converted from the ultrasound wave;
a signal processing section that carries out signal processing to the digital echo signal;
a processing-speed changing section that changes an operation frequency of the signal processing in the signal processing section; and
a change control section that controls change of the operation frequency in the processing-speed changing section.

An ultrasound diagnostic system according to an embodiment of the present invention includes an electronic scan ultrasound probe having an electronic scan ultrasound transducer mounted therein;
a mechanical scan ultrasound probe having a mechanical scan ultrasound transducer mounted therein;
a connection section to which the electronic scan ultrasound probe and the mechanical scan ultrasound probe are detachably connected, respectively;
a transmission section that drives the ultrasound transducer of the ultrasound probe connected to the connection section by a transmission signal of a transmission frequency thereof;
an echo signal creation section that creates a digital echo signal from an echo signal received by the ultrasound transducer and converted from the ultrasound wave;
a signal processing section that carries out signal processing to the digital echo signal;
a processing-speed changing section that changes an operation frequency of the signal processing in the signal processing section; and
a change control section that controls change of the operation frequency in the processing-speed changing section.

DETAILED DESCRIPTION OF THE PREFERRED EMBODIMENTS

Embodiments of the present invention will be described below referring to the attached drawings.

First Embodiment

Prior to specific explanation of the present embodiment, a problem in a prior-art example will be explained.

In a prior-art ultrasound diagnostic apparatus, a transmission frequency of a connected electronic scan ultrasound probe is in a range of 3 to 12 MHz, for example, and a transmission frequency of a connected mechanical scan ultrasound probe is in a range of 5 to 30 MHz, for example, in general.

Therefore, in an ultrasound diagnostic apparatus to which both the electronic scan ultrasound probe and the mechanical scan ultrasound probe can be connected, a signal processing section for processing a received signal should respond to a transmission frequency from a low frequency to a high frequency (3 to 30 MHz, for example).

Here, if the signal processing section is configured by an analog circuit, a circuit scale should become large, which causes the ultrasound diagnostic apparatus to become large.

On the other hand, if the signal processing section is configured by a digital circuit, it is possible to make the circuit scale small, but the analog signal should be converted to digital data using an A/D converter and given signal processing, and in this case, if a sampling clock (equal to an operation frequency of the signal processing section) at the A/D conversion processing by the A/D converter is low, waveform reproducibility is lowered.

Figure 7:
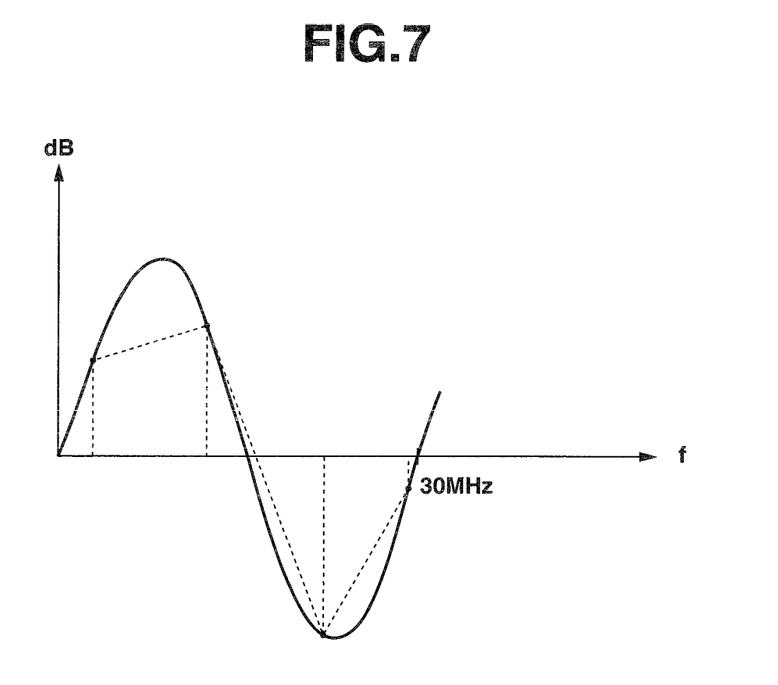
FIG. 7 is an explanatory diagram for explaining a problem in a prior-art signal processing section.

For example, in order to reproduce a received echo signal of 30 MHz, four samples in one cycle is needed at the minimum, and a frequency of the sampling clock of the A/D conversion processing needs to be set at a high speed of 120 MHz. Naturally, the signal processing section in a rear stage of the A/D conversion processing should also be designed to be operated at 120 MHz. (See FIG. 7)

However, there are some filters limiting a receiving band in the signal processing section, and in order to process them at a high speed of 120 MHz, the number of taps constituting a digital filter is limited. For example, the number of taps should be set at 40 or less.

However, in view of nature of the digital filter, it is necessary to increase the number of taps as many as possible in order to realize a steep cut-off characteristic. Thus, if the number of taps is set at 40 or less for high-speed processing at 120 MHz, it becomes difficult to realize a bandpass filter with a steep cut-off of a low center frequency (approximately 3 MHz).

Figure 8:
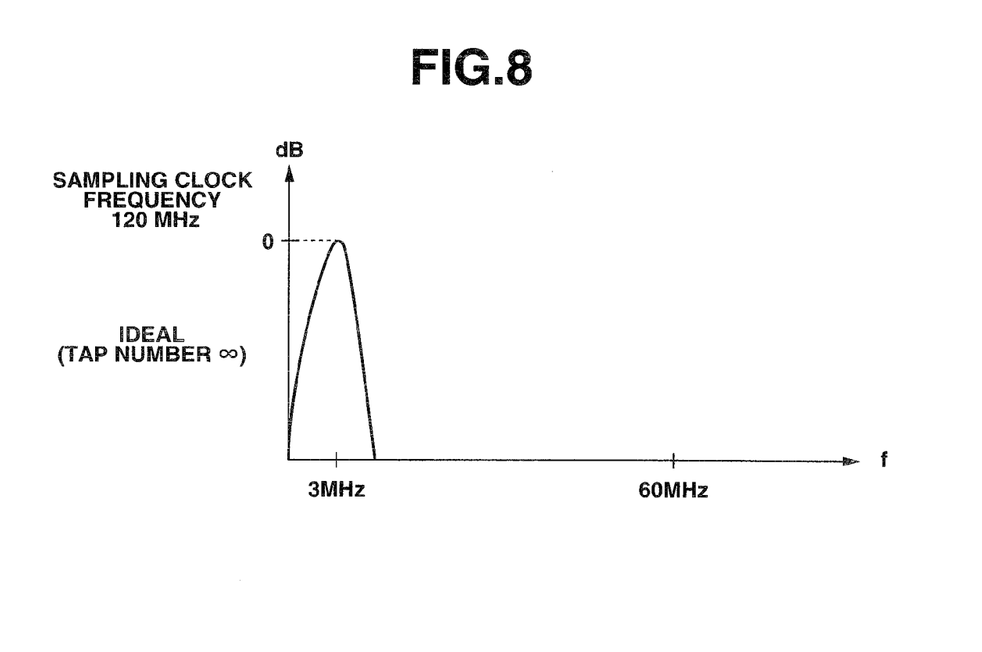
FIG. 8 is a diagram illustrating ideal filter characteristics.
Figure 9:
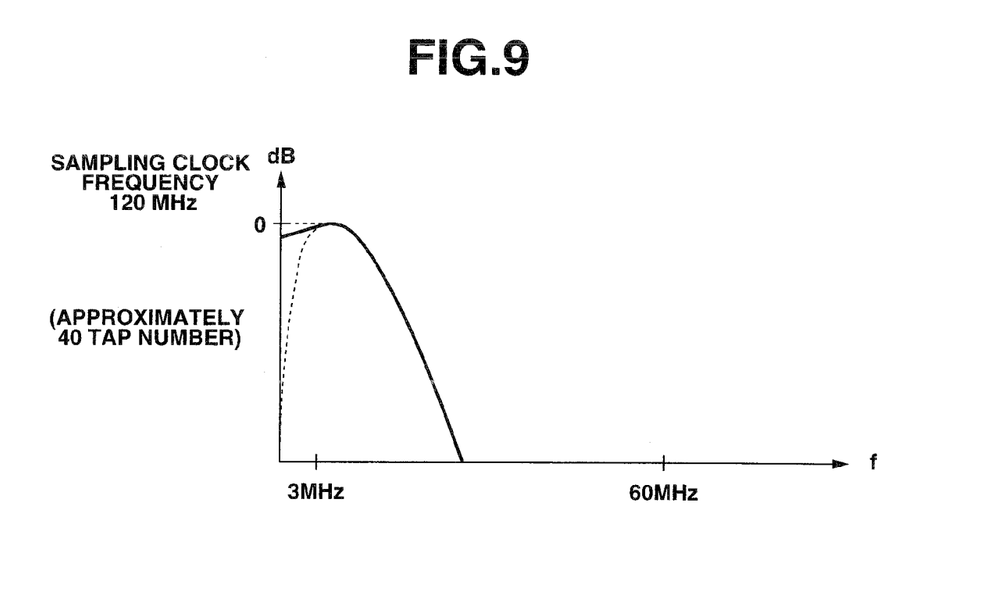
FIG. 9 is a filter characteristic diagram illustrating a state in which a direct current component cannot be fully cut off if the number of taps is limited to the predetermined number.

That is, fine filter adjustment of a low-frequency component becomes difficult, and such a problem occurs that though a characteristic shown by a dotted line portion as in FIG. 9 is desirably realized for an ideal state (FIG. 8) at the infinite tap number, an unnecessary frequency component (direct current component) cannot be fully cut off.

In order to solve such a problem, the signal processing section is preferably configured as a single common signal processing section that can process frequencies from a low frequency to a high frequency, that is, both data of the electronic scan ultrasound probe and the mechanical scan ultrasound probe by constituting an operation frequency (sampling clock of the A/D converter) of the signal processing section changeable so that a circuit scale thereof is made small.

However, though the first and second prior-art examples disclose the signal processing section that can handle both the electronic scan and the mechanical scan and converts the received signal by the A/D converter to the digital data for signal processing, no disclosure or suggestion is made on means and a method for making the circuit scale small by configuring the signal processing section as a single common signal processing section that can process frequencies from a low frequency to a high frequency, that is, both data of the electronic scan ultrasound probe and the mechanical scan ultrasound probe by constituting the operation frequency (sampling clock of the A/D converter) of the signal processing section changeable.

The present embodiment will be explained specifically below.

Figure 1:
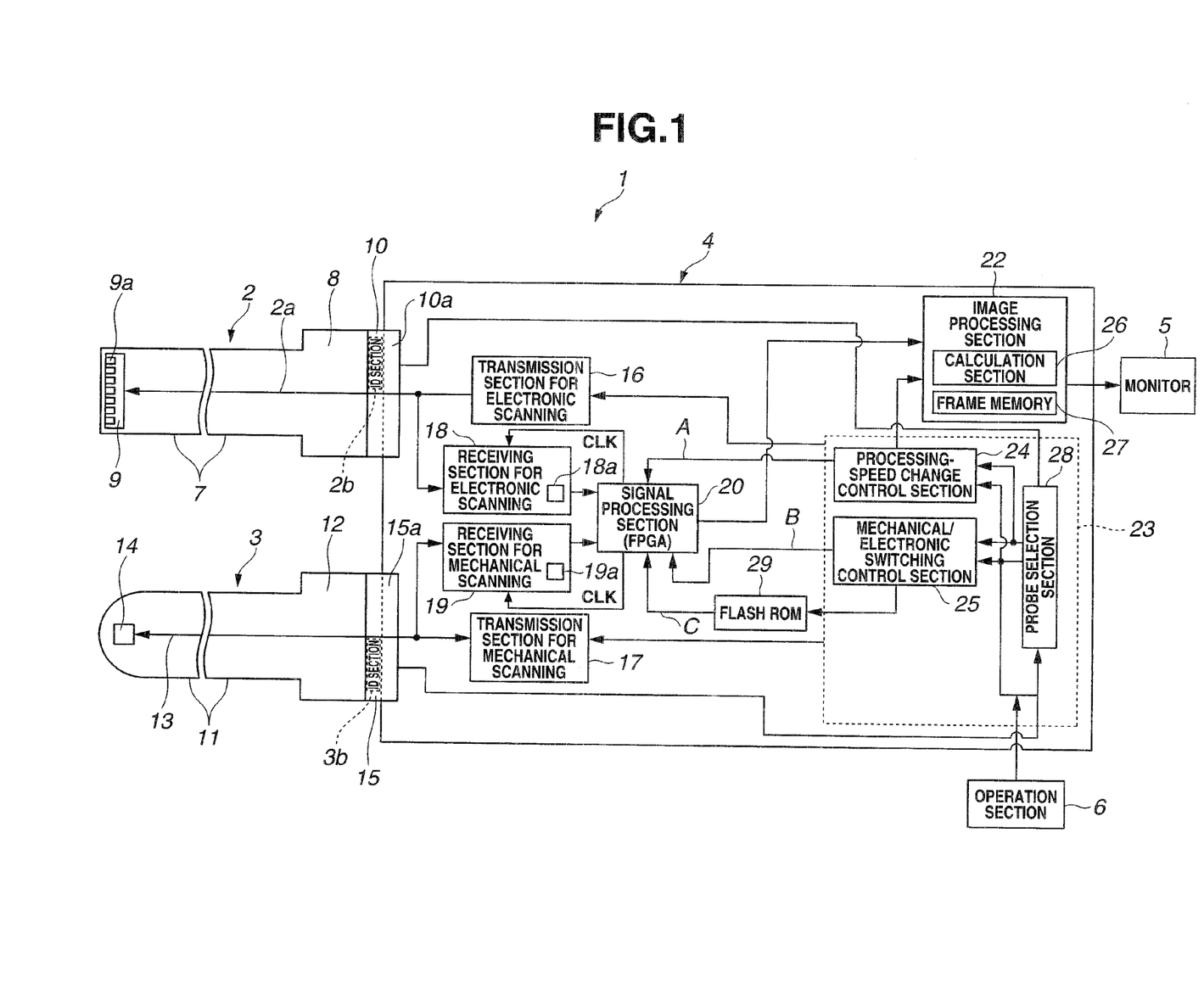
FIG. 1 is a block diagram illustrating an entire configuration of an ultrasound diagnostic system having an ultrasound diagnostic apparatus according to a first embodiment of the present invention.

An ultrasound diagnostic system 1 includes an electronic scan ultrasound probe 2, a mechanical scan ultrasound probe 3, an ultrasound diagnostic apparatus 4 of the present embodiment, a monitor 5, and an operation section 6 as shown in FIG. 1.

In the present embodiment, as shown in FIG. 1, two ultrasound probes of the electronic scan ultrasound probe 2 and the mechanical scan ultrasound probe 3 are connected to the ultrasound diagnostic apparatus 4, but configuration in which either one of the electronic scan ultrasound probe 2 and the mechanical scan ultrasound probe 3 is connected to the ultrasound diagnostic apparatus 4 is also applied to the present invention.

Also, the monitor 5 as the display device is connected to the ultrasound diagnostic apparatus 4, but a display section similar to the monitor 5 may be further provided in the ultrasound diagnostic apparatus 4 in configuration.

The electronic scan ultrasound probe 2 is constituted as an electronic scan ultrasound endoscope, for example, and has an insertion section 7 formed in an elongated shape so as to be easily inserted into a subject and the like and an operation section 8 provided at a rear end of the insertion section 7, and an ultrasound transducer 9 is arranged at a distal end portion of the insertion section 7. The ultrasound transducer 9 is formed by aligning a plurality of transducer elements 9a.

In the operation section 8, a connector 10 to be detachably connected to the ultrasound diagnostic apparatus 4 is provided. In the connector 10, an electric contact section to which a signal line 2a from the ultrasound transducer 9 is connected is provided, though not shown. Also, in the connector 10, an ID section 2b constituted by a memory and the like in which identification information of a probe ID and the like of the electronic scan ultrasound probe 2 is stored, for example, is provided.

The electronic scan ultrasound probe 2 has the ultrasound transducer 9 electrically connected to the ultrasound diagnostic apparatus 4 through the signal line 2a when the connector 10 is connected to the ultrasound diagnostic apparatus 4.

The electronic scan ultrasound probe 2 is connected to a light source device and a video processor, not shown, if it is constituted as an electronic scan ultrasound endoscope, for example. The electronic scan ultrasound probe 2 has an illumination optical system, an objective optical system, and an image pickup section, not shown, provided at the distal end portion of the insertion section 7.

The electronic scan ultrasound probe illuminates inside a body cavity from the illumination optical system by illumination light supplied from the light source device, forms reflected light from the illuminated body cavity inside into a subject image by the objective optical system and picks up a formed optical image by the image pickup section.

The electronic scan ultrasound probe 2 outputs an image pickup signal to the video processor. The video processor processes the image pickup signal and creates a standard video signal and outputs the video signal to a monitor for endoscopic image so that the endoscopic image is displayed on the monitor for endoscopic image.

The mechanical scan ultrasound probe 3 has an insertion section 11 formed in an elongated shape so as to be easily inserted into a subject and the like and an operation section 12 provided at a rear end of the insertion section 11.

The mechanical scan ultrasound probe 3 has an ultrasound transducer 14 mounted at a distal end side of a flexible shaft 13 inserted through the insertion section 11. A rear end of the flexible shaft 13 is connected to a rotation driving section, not shown, disposed at the operation section 12.

The rotation driving section mechanically rotates and drives the ultrasound transducer 14 by rotating the flexible shaft 13 by a motor, not shown. Also, in the rotation driving section, a rotation position detection section for detecting a rotation position such as an encoder and the like, not shown, is provided. A periphery of the ultrasound transducer 14 is filled with an ultrasound propagation medium, not shown, for transmitting (propagating) an ultrasound wave.

In the operation section 12, a connector 15 detachably connected to the ultrasound diagnostic apparatus 4 is provided. In the connector 15, an electric contact section, not shown, to which a signal line from the rotation driving section is connected is provided. Also, in the connector 15, an ID section 3*b* constituted by a memory and the like, for example, in which identification information such as a probe ID and the like of the mechanical scan ultrasound probe 3 is stored is provided.

The mechanical scan ultrasound probe 3 has the ultrasound transducer 14 electrically connected to the ultrasound diagnostic apparatus 4 through the signal line inserted through the flexible shaft 13 when the connector 15 is connected to the ultrasound diagnostic apparatus 4.

Subsequently, specific configuration of the ultrasound diagnostic apparatus 4 of the present embodiment will be described referring to FIGS. 1 to 3.

The ultrasound diagnostic apparatus 4 of the present embodiment generates an ultrasound wave by the ultrasound transducer 9 or 14 of the ultrasound probe 2 or 3 connected thereto, processes a reflected echo signal and creates an ultrasound image and includes a signal processing section 20 that processes digital data of an echo signal of the ultrasound wave obtained from the ultrasound probe 2 or 3 (in other words, digital echo signal) and a processing-speed change control section 24 that controls so that the operation frequency of the signal processing section 20 is changed.

And the processing-speed change control section 24 changes and controls the operation frequency of the signal processing section 20 according to a transmission frequency at which the ultrasound transducer mounted on the electronic scan ultrasound probe 2 or mechanical scan ultrasound probe 3 generates ultrasonic vibrations.

In the electronic scan ultrasound probe 2 or mechanical scan ultrasound probe 3, one of ultrasound transducers with different transmission frequencies (resonance frequencies) generating ultrasound waves according to probe types is mounted.

The ultrasound diagnostic apparatus 4 of the present embodiment can handle either of the electronic scan ultrasound probe 2 and mechanical scan ultrasound probe 3 in which the ultrasound transducers with the different transmission frequencies are mounted. For example, the ultrasound diagnostic apparatus 4 of the present embodiment can generate an ultrasonotomographic image in any case of the transmission frequency of the ultrasound transducer in a range from several MHz to several tens MHz.

With the above configuration, the ultrasound diagnostic apparatus 4 of the present embodiment is constituted as the single common signal processing section 20 that can process both data of the electronic scan ultrasound probe 2 and mechanical scan ultrasound probe 3 and the signal processing section 20 is able to be constituted with a small circuit scale.

Specific configuration will be described. As shown in FIG. 1, the ultrasound diagnostic apparatus 4 includes an electronic-side connector receiving section 10*a*, a mechanical-side connector receiving section 15*a*, a transmission section 16 for electronic scanning, a transmission section 17 for mechanical scanning, a receiving section 18 for electronic scanning, a receiving section 19 for mechanical scanning, the signal processing section 20, an image processing section 22, a control section 23 having the processing-speed change control section 24, and a flash ROM 29.

The operation section 6 connected to the ultrasound diagnostic apparatus 4 is constituted by a track ball, a keyboard and the like capable of input of instructions of a display range of the ultrasound image, instructions of the ultrasound probe to be driven, range switching instructions, and medical information such as patient information required for ultrasound examinations and the like, for example.

The connector 10 of the electronic scan ultrasound probe 2 is detachably connected to the electronic-side connector receiving section 10*a* constituting a first connection section. Thereby, the electronic scan ultrasound probe 2 is detachably connected to the ultrasound diagnostic apparatus 4.

The connector 15 of the mechanical scan ultrasound probe 3 is detachably connected to the mechanical-side connector receiving section 15*a* constituting a second connection section. Thereby, the mechanical scan ultrasound probe 3 is detachably connected to the ultrasound diagnostic apparatus 4.

The electronic-side connector receiving section 10*a* is provided with an electronic-side fitting section having a receiving-side electric contact section contacted and conducted to the electric contact section of the connector 10, though not shown. On the other hand, the mechanical-side connector receiving section 15*a* is provided with a mechanical-side fitting section having a receiving-side electric contact section contacted and conducted to the electric contact section of the connector 15, though not shown.

Each electric contact section of the electronic-side and mechanical-side fitting sections (not shown) is electrically connected to a probe selection section 28 of the control section 23 through the signal line.

And the probe selection section 28 of the control section 23 is conducted to each electric contact section and detects that the connector 10 or the connector 15 is connected when the connector 10 or the connector 15 is fitted in and connected to the electronic-side and mechanical-side fitting sections and at the same time, reads out the identification information such as the probe ID and the like from the ID section 2*b* or the ID section 3*b* and discriminates (identifies) whether the connected ultrasound probe is the electronic scan ultrasound probe 2 or the mechanical scan ultrasound probe 3.

Therefore, the probe selection section 28 has a function as a discrimination section for discriminating whether the connected ultrasound probe is the electronic scan ultrasound probe 2 or the mechanical scan ultrasound probe 3.

Though will be described later, a discrimination result of the probe selection section 28 is outputted to the mechanical/electronic switching control section 25 in the control section 23.

The ultrasound diagnostic apparatus 4 obtains an echo signal from the electronic scan ultrasound probe 2 or the mechanical scan ultrasound probe 3 connected thereto, creates an ultrasonotomographic image on the basis of sound-ray data obtained from the echo signal and displays the ultrasonotomographic image on the monitor 5.

Specifically, the transmission section 16 for electronic scanning applies a pulse-state transmission signal (ultrasound driving signal) with a transmission frequency of the ultrasound transducer 9 to the ultrasound transducer 9 built in the electronic scan ultrasound probe 2 connected to the electronic-side connector receiving section 10*a* for driving. The ultrasound transducer 9 transmits a pulse-state ultrasound wave to a living tissue. In this case, the transmission section 16 for electronic scanning electronically scans the ultrasound wave by sequentially driving the plurality of transducer elements 9*a*.

The pulse-state ultrasound wave reflected from the living tissue side is received by the ultrasound transducer 9 and converted to an echo signal of the ultrasound wave as an electric signal.

The receiving section 18 for electronic scanning constitutes an echo signal creation section for creating a digital echo signal from the echo signal of the ultrasound wave.

For example, the receiving section 18 for electronic scanning is constituted by an A/D converter 18*a* for converting the echo signal to the digital signal and a beamformer for creating sound-ray data in a predetermined direction and the like and outputs electronic scan data as the created digital echo signal to the signal processing section 20.

Also, the transmission section 17 for mechanical scanning applies a pulse-state transmission signal with a transmission frequency of the ultrasound transducer 14 to the ultrasound transducer 14 built in the mechanical scan ultrasound probe 3 connected to the mechanical-side connector receiving section 15*a* for driving. The ultrasound transducer 14 transmits a pulse-state ultrasound wave to a living tissue. In this case, the ultrasound transducer 14 has rotation and the like mechanically scanned, and the ultrasound is mechanically scanned.

The pulse-state ultrasound wave reflected from the living tissue side is received by the ultrasound transducer 14 and converted to an echo signal of the ultrasound wave as an electric signal.

The receiving section 19 for mechanical scanning constitutes an echo signal creation section for creating a digital echo signal from the echo signal of the ultrasound wave.

For example, the receiving section 19 for mechanical scanning is constituted by an A/D converter 19*a* for converting the echo signal to the digital signal and an amplifier for amplifying a signal with a predetermined amplification rate and the like and outputs mechanical scan data as the created digital echo signal to the signal processing section 20.

The signal processing section 20 carries out signal processing to digital data from the receiving section 18 for electronic scanning and the receiving section 19 for mechanical scanning.

For example, the signal processing section 20 creates sound-ray data of luminance information on the basis of the digital data from the receiving section 18 for electronic scanning and the receiving section 19 for mechanical scanning and outputs the data to the image processing section 22.

The image processing section 22 creates a single ultrasound image on a frame memory 27 by carrying out coordinate conversion processing to the sound ray data signal-processed by the signal processing section 20 so as to create pixel data of a pixel position for display on a screen of the monitor 5 using the calculation section 26 and a coordinate conversion table (not shown) under control of the control section 23 constituted by a CPU and the like, for example.

And the image processing section 22 processes the pixel data (also referred to as data for display) for display on the basis of the ultrasound image created for each frame on the frame memory 27 and displays the ultrasound image on the display screen of the monitor 5.

Subsequently, configuration of the signal processing section 20 and the control section 23, which are essential parts of the ultrasound diagnostic apparatus 4 of the present embodiment, will be described.

First, configuration of the signal processing section 20 will be described. As shown in FIG. 2, the signal processing section 20 is constituted by a FPGA (Field Programmable Gate Array) capable of being programmed, for example, and has a multiplexer (hereinafter referred to as MUX) 30 into which digital data from the receiving section 18 for electronic scanning and the receiving section 19 for mechanical scanning is inputted and which outputs either one of the data, a signal processing circuit 31 for signal processing of the output data from the MUX 30 and having an internal RAM 31A inside as an internal storage section capable of rewriting a coefficient of a tracking filter 36, and a processing-speed changing circuit 32 that supplies a clock signal (described as CLK in FIG. 2) on the basis of a control signal A from the processing-speed change control section 24 of the control section 23, which will be described later, so as to switch operation frequencies of the MUX 30 and the signal processing circuit 31 and to change the respective processing speeds. Specific configuration of the signal processing circuit 31 will be described later.

Subsequently, the control section 23 will be described. As shown in FIG. 1, the control section 23 includes the processing-speed change control section 24, the mechanical/electronic switching control section 25, and the probe selection section 28. The flash ROM 29 is connected to the mechanical/electronic switching control section 25.

The processing-speed change control section 24, the mechanical/electronic switching control section 25, the flash ROM 29; and the probe selection section 28 constitute the change control section.

The flash ROM 29 stores filter coefficients of the tracking filter 36 in the signal processing circuit 31, which will be described later, corresponding to the electronic scan ultrasound probe 2 and the mechanical scan ultrasound probe 3.

Also, each filter coefficient stored in the flash ROM 29 is read out by the mechanical/electronic switching control section 25 on the basis of a detection result by the probe selection section 28 and then, written in the internal RAM 31A in the signal processing circuit 31 of the signal processing section 20. The plurality of filter coefficients read out of the flash ROM 29 and written in the internal RAM 31A are indicated by a symbol C.

Each filter coefficient stored in the flash ROM 29 can be freely rewritten by executing an application by control of the control section 23.

In the present embodiment, the probe selection section 28 of the control section 23 discriminates whether the connected ultrasound probe is the electronic scan ultrasound probe 2 or the mechanical scan ultrasound probe 3 on the basis of the read-out information such as the probe ID and the like from the ID section 2b or the ID section 3b and outputs a discrimination result to the processing-speed change control section 24 and the mechanical/electronic switching control section 25.

For example, if both the electronic and mechanical scan probes are connected, either ultrasound probe may be selected by inputting information indicating the connected ultrasound probe by the operation section 6 without using the discrimination result from the probe selection section 28, and the information may be outputted as the discrimination result to the processing-speed change control section 24 and the mechanical/electronic switching control section 25.

Figure 2:
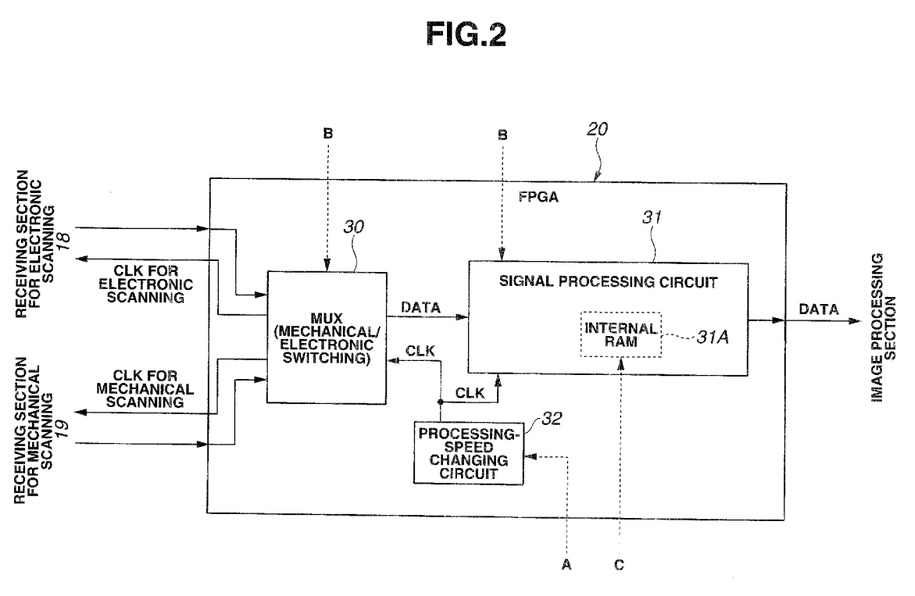
FIG. 2 is a block diagram illustrating a specific configuration of a signal processing section of the ultrasound diagnostic apparatus in FIG. 1.

The mechanical/electronic switching control section 25 outputs a control signal B for controlling switching of the MUX 30 and the signal processing circuit 31 in the signal processing section 20 shown in FIG. 2 on the basis of the supplied discrimination result so that the processing is executed to the electronic scan ultrasound probe 2 or the mechanical scan ultrasound probe 3 on the basis of the discrimination result.

That is, as shown in FIG. 2, if the probe ID is the electronic scan ultrasound probe 2, the MUX 30 outputs electronic scan data to the signal processing circuit 31. On the other hand, if the probe ID is the mechanical scan ultrasound probe 3, the MUX 30 outputs mechanical scan data to the signal processing circuit 31.

At the same time, if the probe ID is the electronic scan ultrasound probe 2, the signal processing circuit 31 executes processing through a mechanical/electronic B-mode processing circuit 33 (See FIG. 3) or an electronic Doppler processing circuit 34 (See FIG. 3) in the signal processing circuit 31, which has been converted to a processing speed corresponding to the electronic scan ultrasound probe 2 and outputs the electronic scan data to the image processing section 22.

On the other hand, if the probe ID is the mechanical scan ultrasound probe 3, the signal processing circuit 31 executes processing through a mechanical/electronic B-mode processing circuit 33 (See FIG. 3) in the signal processing circuit 31, which has been converted to a processing speed corresponding to the mechanical scan ultrasound probe 3 and outputs the mechanical scan data to the image processing section 22.

Also, the mechanical/electronic switching control section 25 executes control so that each filter coefficient stored in the flash ROM 29 is read out on the basis of the probe ID and written in the internal RAM 31A in the signal processing circuit 31.

An operation on the basis of each filter coefficient written in the internal RAM 31A in the signal processing circuit 31 will be described later.

In the present embodiment, the processing-speed change control section 24 changes and controls the operation frequency of the signal processing section 20 according to the transmission frequency of the ultrasound transducer mounted in the ultrasound probe on the basis of the discrimination result of the probe selection section 28.

Specifically, the processing-speed change control section 24 outputs the control signal A for changing and controlling the operation frequency of the signal processing section 20 according to the transmission frequency of the ultrasound transducer mounted in the ultrasound probe on the basis of the discrimination result (probe ID) to the processing-speed changing circuit 32 shown in FIG. 2.

The processing-speed changing circuit 32 creates CLK on the basis of the control signal A from the processing-speed change control section 24, switches the operation frequencies of the MUX 30 and the signal processing circuit 31 using the CLK and controls so that the respective processing speeds are changed.

For example, the processing-speed changing circuit 32 changes the frequency of the CLK to be created on the basis of the control signal A from the processing-speed change control section 24. In this case, the processing-speed changing circuit 32 creates the CLK of the frequency roughly in proportion to the transmission frequency of the ultrasound transducer, for example. And the operation frequency of the signal processing section 20 for carrying out the signal processing operation is changed in synchronization with the CLK by changing the frequency of the CLK.

Here, considering the characteristics of the ultrasound wave generated by the ultrasound transducer, the ultrasound wave has such a characteristic that the wave reaches the farther with the lower frequency, while the wave is reflected and returned only from a certain point within a short-distance range in the case of a high frequency.

Therefore, it is necessary to set an optimal filter according to each distance in the signal processing section 20. Thus, it is necessary to switch the filter characteristic per a certain distance.

Figure 3:
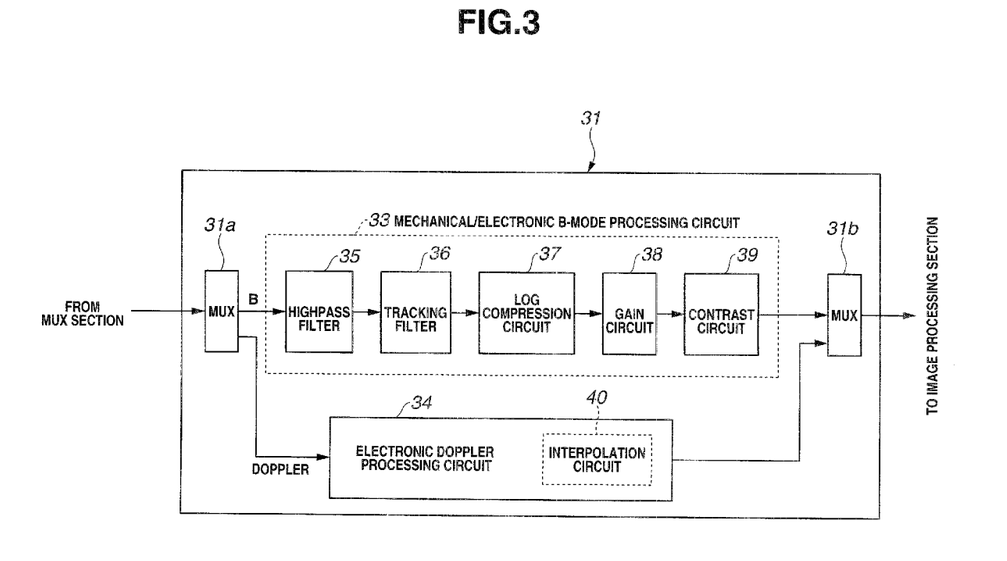
FIG. 3 is a block diagram illustrating a specific configuration of a signal processing circuit in the signal processing section in FIG. 2.
Figure 4:
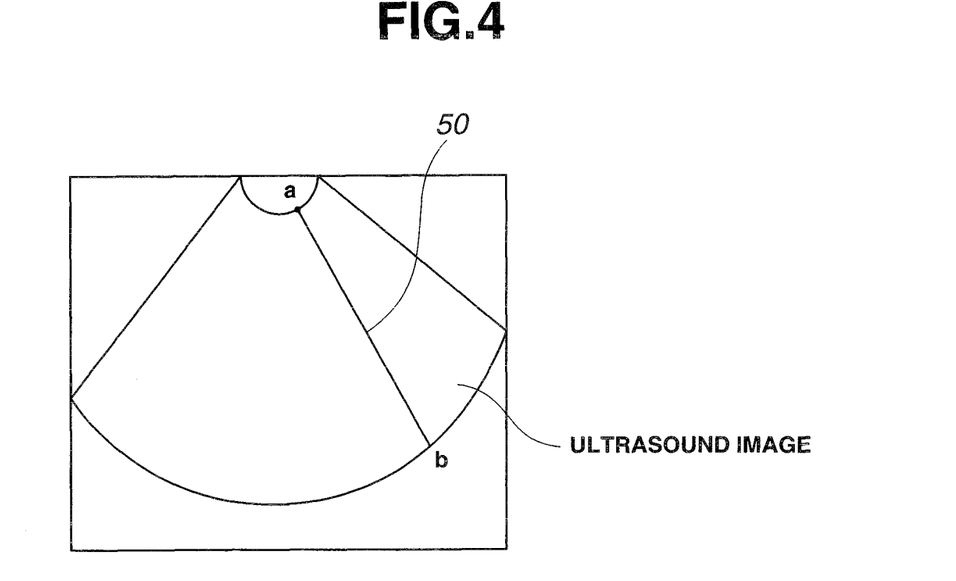
FIG. 4 is an explanatory diagram for explaining one sound-ray data in an ultrasound image created by the ultrasound diagnostic apparatus.

Then, in the present embodiment, for example, if one sound-ray data 50 of the ultrasonotomographic image has a length (distance) between a to b as shown in FIG. 4, a tracking filter 36 (See FIG. 3) in the signal processing circuit 31 divides a distance from a to b of the one sound-ray data to each predetermined distance region interval (t1 to t6 . . . ), and by setting each filter coefficient written in the internal RAM 31A in advance for each predetermined distance region interval (t1 to t6), respectively, a plurality of filter 1 to filter 6 . . . whose filter characteristics are switched for each predetermined distance region interval (t1 to t6) are provided.

That is, the predetermined distance region interval (t1 to t6) indicates timing to switch the filter characteristic of the tracking filter 36.

In the present embodiment, the tracking filter 36 is realized by switching a coefficient of a fixed filter. In this case, switching of the filter characteristic of the tracking filter 36, that is, switching of each filter coefficient is executed based on a CLK supplied by the processing-speed changing circuit 32 so that all the filter coefficients are switched based on the CLK. In addition, the switching of each filter coefficient is executed in a cycle T of the CLK or within a time period shorter than the cycle T. In this embodiment, when the frequency of the CLK is assumed to be FCLK, the cycle T is defined by the following expression.

$$T = 1/\text{FCLK}$$

In the present embodiment, a switching position of the tracking filter 36 is fixed (fixed to the predetermined region interval (t1 to t6 . . . )) not by the transmission frequency of the ultrasound probe.

Moreover, the filter characteristics of the tracking filter 36 can be easily changed by writing each filter coefficient read out of the flash ROM 29 in the internal RAM 31A in the signal processing circuit 31 on the basis of the probe ID for change.

Also, in the present embodiment, the signal processing section 20 is devised for the optimal processing to both data of the electronic scan ultrasound probe 2 and the mechanical scan ultrasound probe 3. Specific configuration of the signal processing section 20 will be described referring to FIG. 3.

As shown in FIG. 3, the signal processing circuit 31 of the signal processing section 20 includes a MUX 31a for switching input data, the mechanical/electronic B-mode processing circuit 33 in which processing circuits are made common in order to handle both data of the electronic scan ultrasound probe 2 and the mechanical scan ultrasound probe 3, the electronic Doppler processing circuit 34, and a MUX 31b for switching output data.

The MUX 31a switches and outputs the inputted electronic scan data to the mechanical/electronic B-mode processing circuit 33 or the electronic Doppler processing circuit 34 under the switching control by the mechanical/electronic switching control section 25 if the connected ultrasound probe is the electronic scan ultrasound probe 2.

Also, if the MUX 31a determines a B mode in determination between the B mode or a Doppler mode on the basis of head information of the data, the electronic scan data is outputted to the mechanical/electronic B-mode processing circuit 33, while if the MUX determines the Doppler mode, the electronic scan data is outputted to the electronic Doppler processing circuit 34.

Moreover, the mechanical/electronic B-mode processing circuit 33 includes a highpass filter 35 for cutting a direct current component and a low frequency, the tracking filter 36 arranged in a rear stage of the highpass filter 35, a LOG compression circuit 37 for carrying out LOG compression processing of output data of the tracking filter 36, a gain circuit 38 for adjusting a gain of the output data of the LOG compression circuit 37, a contrast circuit 39 for contrast adjustment of the output data of the gain circuit 38 and the like, for example. The mechanical/electronic B-mode processing circuit 33 is not limited to the configuration shown in FIG. 3.

Since the highpass filter 35 for cutting the direct current component and the low frequency is provided in a front stage of the tracking filter 36, it is possible to attenuate the direct current component by approximately 40 dB with respect to a passband signal, for example.

As mentioned above, even though the tracking filter 36 can singularly switch to an optimal filter characteristic from a low frequency to a high frequency, the characteristic permits an unnecessary low frequency component to pass through and cannot fully remove the direct current component due to the limitation on the number of taps.

Figure 5:
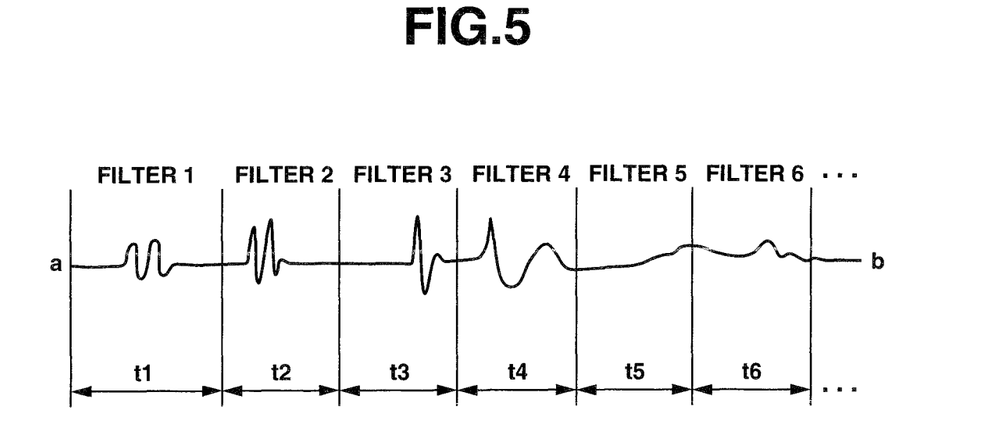
FIG. 5 is an explanatory diagram for explaining timing when a filter is switched according to a signal for each predetermined interval in the one sound-ray data.

Then, since the filter is different for each predetermined distance interval of the filter 1, the filter 2, the filter 3, . . . shown in FIG. 5, an attenuation amount of the direct current component would be different.

Thus, brightness of a background on the ultrasound image becomes different such that a predetermined distance region of the filter 1 is dark but the predetermined distance region of the filter 2 is bright and the like, for example.

Then, in the present embodiment, the highpass filter 35 having a characteristic to fully attenuate the direct current component and the unnecessary low frequency component in the front stage of the tracking filter 36 is provided as above so that the direct current component does not exert an influence.

Also, the LOG compression circuit 37 as a compression processing section of a logarithmic characteristic is constituted by a look-up table (LUT) and has a characteristic to have a relation of an input bit width>an output bit width.

In the present embodiment, the mechanical/electronic B-mode processing circuit 33 constituting a circuit common to the electronic scan and the mechanical scan has the same bit numbers of input/output of a module even if the electronic scan ultrasound probe 2 and the mechanical scan ultrasound probe 3 are connected so that both data of mechanical scan and electronic scan can be processed.

Also, the electronic Doppler processing circuit 34 has an interpolation circuit 40 for creating interpolation sound-ray data from Doppler data of an obtained actual sound ray. The interpolation circuit 40 can create weighted interpolation sound-ray data by executing non-linear interpolation processing and the like in interpolation calculation. As a result, resolution of a Doppler image reflecting information of a blood flow can be improved while frame rate is improved or maintained.

Therefore, according to a first embodiment, by constituting the operation frequency of the signal processing section 20 changeable, the ultrasound diagnostic apparatus 4 in which the signal processing section 20 can be configured as a single common signal processing section that can process both data of the electronic scan ultrasound probe 2 and the mechanical scan ultrasound probe 3 and the signal processing section 20 can be realized in a small circuit scale can be provided.

Second Embodiment

Figure 6:
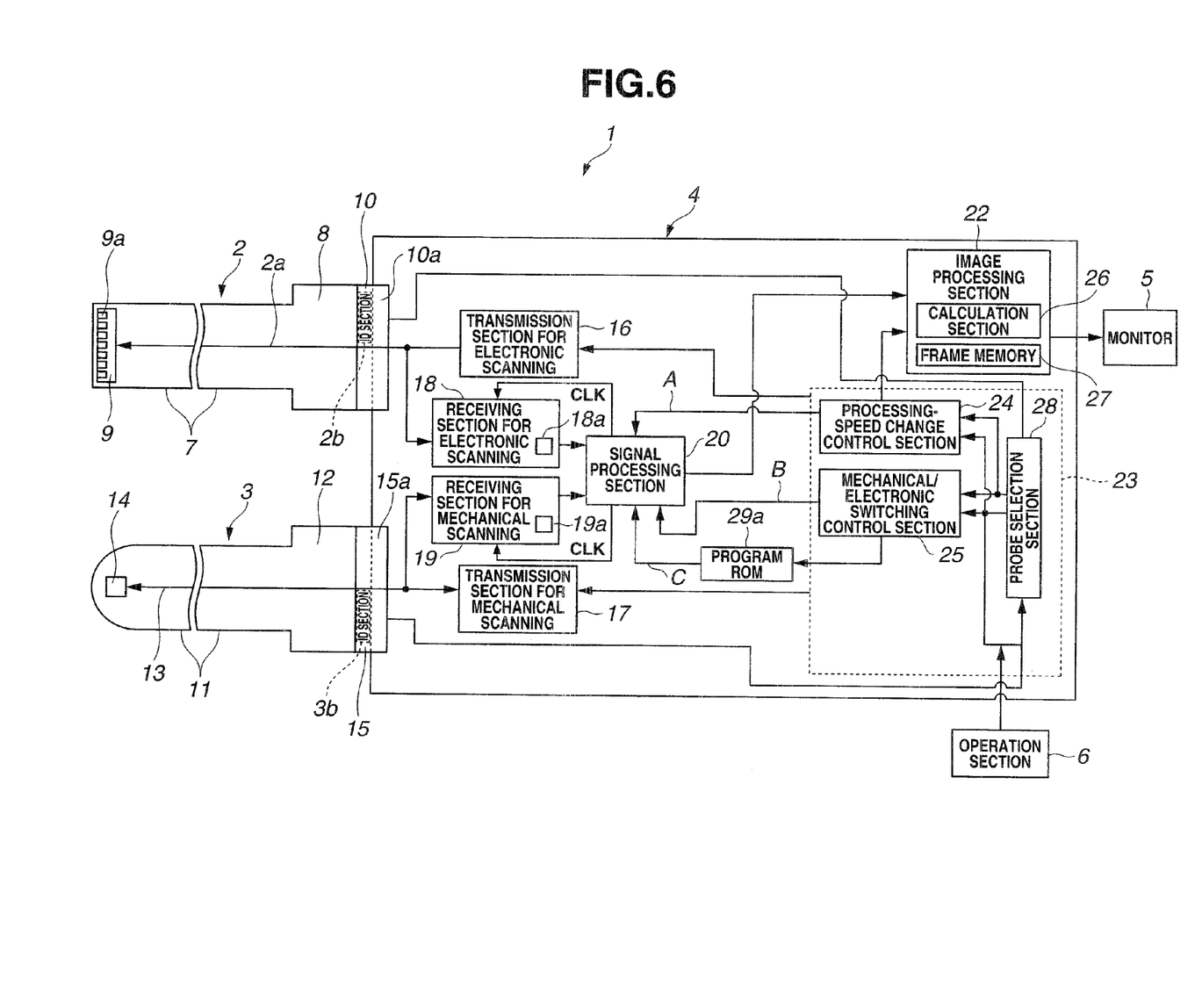
FIG. 6 is a block diagram illustrating an entire configuration of an ultrasound diagnostic system having an ultrasound diagnostic apparatus according to a second embodiment of the present invention.

FIG. 6 is a block diagram illustrating an entire configuration of an ultrasound diagnostic apparatus having an ultrasound observing device according to a second embodiment of the present invention. The same reference numerals are given to constituent elements similar to those in the first embodiment and only different portions will be described in FIG. 6.

As shown in FIG. 6, the ultrasound diagnostic apparatus 4 of the second embodiment is configured substantially similar to the configuration of the first embodiment but is configured having a program ROM 29a instead of the flash ROM 29.

The program ROM 29a stores programs for executing optimal signal processing to the electronic scan ultrasound probe 2 and the mechanical scan ultrasound probe 3, respectively.

The signal processing section 20 is configured by a programmable FPGA. And the mechanical/electronic switching control section 25 reads out a corresponding program stored in the program ROM 29a on the basis of a discrimination result from the probe selection section 28 or input information from the operation section 6 and re-programs the FPGA constituting the signal processing section 20.

In this case, since re-programming is started on the basis of the discrimination result from the probe selection section 28 or the input information from the operation section 6, the re-programming is executed at connection change of the electronic scan or the mechanical scan ultrasound probe.

In the second embodiment, configuration provided with the program ROM 29a instead of the flash ROM 29 in the first embodiment has been explained, but it may be so configured that the flash ROM 29 is not deleted as in the first embodiment but used along with the program ROM 29a.

The other configurations and actions are the same as those in the first embodiment.

Therefore, according to the second embodiment, the same effect as that of the first embodiment can be obtained.

The present invention is not limited only to the above-mentioned embodiments and variations but can be deformed in various ways and can be put into practice in a range not departing from the gist of the invention.

What is claimed is:

1. An ultrasound diagnostic apparatus comprising:
a connection section comprising:
a first connection section configured for detachable connection with an electronic scan ultrasound probe; and
a second connection section configured for detachable connection with a mechanical scan ultrasound probe, wherein the electronic scan ultrasound probe and the mechanical scan ultrasound probe each have an ultrasound transducer with a mutually different transmission frequency for transmitting an ultrasound wave mounted therein;

a transmission section configured to drive the ultrasound transducer of the electronic scan ultrasound probe connected to the first connection section or the ultrasound transducer of the mechanical scan ultrasound probe connected to the second connection section by a transmission signal of a transmission frequency thereof;

an echo signal creation section configured to create a digital echo signal from an echo signal received by the ultrasound transducer of the electronic scan ultrasound probe connected to the first connection section and converted from the ultrasound wave or received by the ultrasound transducer of the mechanical scan ultrasound probe connected to the second connection section and converted from the ultrasound wave;

a signal processing section configured to carry out signal processing of the digital echo signal using a filter;

a processing-speed changing section configured to change an operation frequency of the signal processing in the signal processing section to a frequency corresponding to the transmission frequency of the ultrasound transducer of the electronic scan ultrasound probe connected to the first connection section or the ultrasound transducer of the mechanical scan ultrasound probe connected to the second connection section;

a change control section configured to control change of the operation frequency in the processing-speed changing section to the frequency corresponding to the transmission frequency of the ultrasound transducer of the electronic scan ultrasound probe connected to the first connection section or the ultrasound transducer of the mechanical scan ultrasound probe connected to the second connection section;

a clock frequency changing section configured to change a clock frequency according to the transmission frequency;

a tracking filter provided in the signal processing section and configured to carry out filter processing for each predetermined distance of ultrasound wave propagation in the digital echo signal;

a filter coefficient storage section configured to store a plurality of filter coefficients for constituting the tracking filter;

a discrimination section configured to discriminate the transmission frequency of the ultrasound transducer of the electronic scan ultrasound probe connected to the first connection section or the ultrasound transducer of the mechanical scan ultrasound probe connected to the second connection section; and a tracking filter setting section configured to read out from the filter coefficient storage section a filter coefficient in accordance with a discrimination result by the discrimination section, and set the tracking filter using the filter coefficient corresponding to the transmission frequency, wherein the change control section is further configured to change, in accordance with the discrimination result by the discrimination section, the operation frequency of the signal processing section in synchronization with the clock frequency so as to be equal to the frequency corresponding to the transmission frequency of the ultrasound transducer of the electronic scan ultrasound probe connected to the first connection section or the ultrasound transducer of the mechanical scan ultrasound probe connected to the second connection section.

2. The ultrasound diagnostic apparatus according to claim 1, wherein the signal processing section is further configured to carry out signal processing common to the electronic scan ultrasound probe connected to the first connection section and the mechanical scan ultrasound probe connected to the second connection section.

3. The ultrasound diagnostic apparatus according to claim 2, wherein the signal processing section further comprises, on a front stage side of the tracking filter, a highpass filter configured to cut off a frequency component on a low region side including a direct current so as to be connected in series with the tracking filter.

4. The ultrasound diagnostic apparatus according to claim 2, wherein the signal processing section further comprises a logarithmic compression section configured to logarithmically compress a digital input signal.

5. The ultrasound diagnostic apparatus according to claim 2, wherein:

the signal processing section further comprises an internal storage section configured to write therein the filter coefficient for each of the plurality of predetermined distances of the tracking filter, and the change control section is further configured to read out the plurality of filter coefficients from the filter coefficient storage section according to the ultrasound transducer of the electronic scan ultrasound probe connected to the first connection section or the ultrasound transducer of the mechanical scan ultrasound probe connected to the second connection section, to write the filter coefficients in the internal storage section of the signal processing section, and to set a filter coefficient for each of a plurality of predetermined regions of the tracking filter.

6. The ultrasound diagnostic apparatus according to claim 1, wherein:

the signal processing section is configured by a programmable FPGA (Field Programmable Gate Array), and the FPGA constructs the signal processing section by programming through reading-out of corresponding program data from a storage section in which the program data is stored in advance according to the electronic scan ultrasound probe connected to the first connection section or the ultrasound transducer of the mechanical scan ultrasound probe connected to the second connection section.

* * * * *